(12) United States Patent  (10) Patent No.: US 6,712,823 B2
Grusin et al.  (45) Date of Patent: Mar. 30, 2004

(54) HUMERAL HEAD RESECTION GUIDE

(75) Inventors: N. Kelley Grusin, Memphis, TN (US); Lauralan Terrill-Grisoni, Cordova, TN (US); Charles Sorbie, Kingston (CA); William J. Mallon, Arlington, TN (US); Stuart Patterson, Winter Haven, FL (US); Christopher Jobe, Redland, CA (US)

(73) Assignee: Wright Medical Technology Inc., Arlington, TN (US)

( * ) Notice: Subject to any disclaimer, the term of this patent is extended or adjusted under 35 U.S.C. 154(b) by 85 days.

(21) Appl. No.: 10/043,826

(22) Filed: Jan. 11, 2002

(65) Prior Publication Data

US 2003/0114859 A1 Jun. 19, 2003

Related U.S. Application Data

(60) Provisional application No. 60/340,173, filed on Dec. 14, 2001.

(51) Int. Cl.$^7$ .................................................. A61F 5/00
(52) U.S. Cl. .............................. 606/87; 606/82; 606/62; 606/88
(58) Field of Search .............................. 606/87, 82, 62, 606/63, 64, 65, 67, 79, 86, 88, 89, 96, 102

(56) References Cited

U.S. PATENT DOCUMENTS

| 4,893,619 | A | * | 1/1990 | Dale et al. ..................... 606/87 |
| 4,952,213 | A | * | 8/1990 | Bowman et al. ............... 606/79 |
| 5,108,396 | A | * | 4/1992 | Lackey et al. ................. 606/62 |
| 5,342,368 | A | * | 8/1994 | Petersen ........................ 606/88 |
| 5,364,401 | A | * | 11/1994 | Ferrante et al. ................ 606/84 |
| 5,578,039 | A | * | 11/1996 | Vendrely et al. .............. 606/88 |
| 6,258,095 | B1 | * | 7/2001 | Lombardo et al. ............ 606/88 |
| 6,503,255 | B1 | * | 1/2003 | Albrektsson et al. ......... 606/89 |
| 6,551,324 | B2 | * | 4/2003 | Muller .......................... 606/88 |

* cited by examiner

*Primary Examiner*—Pedro Philogene
(74) *Attorney, Agent, or Firm*—Steven M. Reiss

(57) ABSTRACT

An apparatus for guiding the resection of the head of a humerus is provided. The apparatus includes a base, a cut block, and a stylus. The guide is used in connection with a reamer or other tool that is inserted into the intramedullary mayal of the humerus with the shank of the reamer extending superiorally above the head of the humerus to establish the axis of the humerus. The base is in rotatable connection with the reamer. The cut block is removably attached to the guide and has a component for receiving a saw blade. The stylus attaches to the cut block, preferably by engaging the component for receiving the saw blade, and extends around the articular margin of the humeral head to aid in setting height and version.

24 Claims, 3 Drawing Sheets

HUMERAL HEAD RESECTION GUIDE

This application claims the benefit of Provisional Application No. 60/340,173, filed Dec. 14, 2001.

FIELD OF THE INVENTION

The present invention provides a humeral head resection guide. Specifically, this invention relates to a guide to position a cutting blade at a set angle and height for correct orientation of the osteotomy cut of the head of the humerus with respect to the humeral intramedullary axis.

BACKGROUND OF THE INVENTION

The humerus is a long bone of the upper limb which forms the shoulder joint at its proximal end, where its head articulates with the glenoid cavity of the scapula. The head is nearly hemispherical in form, generally smooth and rounded, and coated with a smooth, durable covering of articular cartilage. The head articulates with the glenoid fossa of the scapula as a ball and socket joint; the joint being lined with a thin, inner lining, the synovium, for smooth movement. The ball and socket joint enables raising, twisting, bending, and forward, side, and backward movement of the arm. Muscles and tendons surrounding the joint provide stability and support.

Arthritis or other degenerative joint diseases may cause the joint surface, e.g. the surface of the humeral head, to be destroyed by wear and tear, inflammation, injury, or previous surgery. Such joint destruction causes the shoulder to become stiff, painful and generally unable to carry out its normal functions. Joint destruction may also be caused by fractures. Whatever the origin, joint damage in the shoulder may necessitate resection and replacement of the humeral head with a prosthetic device.

The goal of shoulder replacement arthroplasty is to restore the best possible function to the joint by removing scar tissue, balancing muscles, and reconstructing the destroyed joint surfaces with artificial ones. Prosthetic implant devices for use in reconstructing the proximal area of the humerus are designed to mimic the natural bone anatomy of the proximal end of the humerus. The prostheses often are modular and include a stem to be fitted to a resected humerus and a head sized and configured to approximate the humeral head. Optionally, one or more connecting members may be used to connect the stem to the head in a variety of configurations. The head portion of the prosthesis generally extends angularly from the stem portion, and the angle and length of the extension may be modified with the connecting members. It is noted, of course, that unitary prostheses or modular prostheses comprising only stem and head components are also used.

The humeral head component of a prosthesis typically has a generally spherical surface on one side and a flat face on the opposite side. The spherical surface replaces the bearing surface of the normal humeral head to allow movement of the shoulder.

It is frequently difficult to establish the proper position and orientation for the implant in the humerus. The surgery to implant a humeral prosthesis involves performance of an osteotomy to accommodate the size and structure of the prosthesis. The osteotomy cut must be made as precisely as possible so that the angle of the cut corresponds to the angle between the stem and head components of the prosthesis. In addition, the rotation of the cut may vary to adjust to bone wear or capsular looseness. Another important variable in proper positioning of the humeral head component is the rotational position, or retroversion, of the head on the humerus. Anatomically, the average retroversion between a plane defined by the perimeter of the anatomical head and the axis of the flexed forearm is approximately 30 degrees. Typically, it has been difficult to reliably reproduce desired retroversion. Establishing correct retroversion is important because incorrect retroversion may lead to problems with subsequent joint dislocation. It is also necessary to establish the correct height of the implant on the humeral shaft. Excess height may create too much tension in the deltoid muscle, while inserting the implant too far down the humerus may result in deltoid lag.

From a surgical standpoint, the humeral head osteotomy cut may be guided by a resection guide. A trial prosthesis may also be placed along the proximal humeral shaft as a guide for proper inclination of the osteotomy. The possibility of error inherent in this free hand approach makes it problematic. Inaccurate resection, even by a small amount, may result in an ill-fitting prosthesis which may cause complications for the patient and may eventually require replacement of the prosthetic device.

Humeral cutting guides have been introduced that aid in the resection of the humeral head. One such cutting guide is disclosed in U.S. Pat. No. 5,108,396 for INTRAMEDULLARY REFERENCED HUMERAL HEAD RESECTION GUIDE, Lackey et al. The guide includes an intramedullary alignment member having a longitudinal axis and structured for substantial axial alignment with the intramedullary canal of the bone. The guide also includes an extramedullary alignment member and a collar rotatably mounted on the intramedullary alignment member for rotating the extramedullary alignment member about the longitudinal axis of the intramedullary alignment member. This rotation allows the extramedullary alignment member to provide a guide for a desired degree of humeral retrotorsion by manipulating the patient's forearm so that it is substantially parallel to the extramedullary alignment member. A cut block and a first shaft and a second shaft in a perpendicular orientation relative to the first shaft for positioning the cut block in a desired orientation relative to the head of the bone are also provided.

Another guide is disclosed Dale et al. in U.S. Pat. No. 4,893,619 for HUMERAL OSTEOTOMY GUIDE. The device includes a proximal end saw guide for defining an osteotomy saw line on the proximal end of the humerus and a distal end mechanism for stably aligning the saw guide on the proximal end of the humerus, such as a distal cross arm having a slot therethrough. The saw guide engages a selected surface on the proximal end of the humerus and supports the proximal end of a radial arm above the humerus. The mechanism for aligning, or cross arm, engages the distal end of the humerus and supports the distal end of the radial arm above the humerus.

U.S. Pat. No. 5,961,555 for MODULAR SHOULDER PROSTHESIS to Huebner discloses a targeting/installation instrument and a modular shoulder prosthesis including a head and a stem. The instrument includes a template member to which are mounted a mounting bar, a height adjusting mechanism, and a retroversion guide. This establishes the correct alignment between the template and the implant. It is noted that the guide is aimed primarily at placing the prosthesis after the cut has been made.

Further, U.S. Pat. No. 6,168,627 for SHOULDER PROSTHESIS, Huebner discloses a shoulder prosthesis including a shoulder prosthesis having a head and an elongate stem portion including a proximal end, a distal section, and an alignment section. The alignment section includes a plurality of reference marks positioned to facilitate placement of the prosthesis in the bone at a previously determined position. A targeting/installation instrument is provided substantially as disclosed in the '555 patent. Additionally, installation and alignment of the implant may be facilitated by placing indications or reference marks on the implant.

SUMMARY OF THE INVENTION

The present invention relates to an apparatus for guiding the resection of the head of the humerus. Specifically, the invention relates to a humeral resection guide that holds a cutting blade at a set angle and position for removing the humeral head. In a preferred embodiment, the guide includes a base, a cut block, and a stylus. The base is configured for rotatable connection with a tool defining the axis of the humerus. The tool may be a reamer or other device that is inserted into the intramedullary canal of the humerus with a shank of the tool extending superiorally above the head of the humerus to establish the axis of the humerus. A cut block is operatively connected to the base and includes a component for receiving a saw blade. A stylus is provided to engage the cut block and extend around the articular margin of the humeral head for alignment with the superior and posterior margins of the humeral head. Optionally, a version gauge may be provided.

The base of the resection guide is configured to be inserted over the shank of the reamer or tool. Preferably, the base includes a bore for receipt of the shank. The base is rotatable about the axis of the humerus, as defined by the reamer or tool, and may be rotated slightly about the axis to provide the proper amount of humeral version. A version gauge may be provided to reference for precise alignment of the base for rotation. The base includes an outwardly and downwardly extending arm, the downwardly extending portion of the arm being roughly parallel to but spaced from the axis of the reamer. Attached to the bottom of the downwardly extending arm of the base is the cut block, the latter having a component for attachment to or receiving of a surgical saw blade. This component may be a slot for receiving and guiding a surgical saw blade.

The cut block is configured for fixation to the humerus, for example, by having a number of small openings through which pins may be inserted. The stylus attaches to the cut block and extends around the articular margin of the humeral head. Any suitable attachment of the stylus to the cut block may be used. Preferably, the stylus attachment includes a tab of the stylus extending into a saw-receiving slot of the cut block. The section of the stylus extending around the articular margin of the humeral head includes a portion for alignment with the superior margin of the humeral head, and another portion for alignment with the posterior margin of the humeral head. The portions for alignment may comprise fiducial tabs.

By rotating the base about the axis; moving the base upwardly and downwardly on the axis; and adjusting the position of the stylus, for example by moving the tab inwardly and outwardly of the saw blade slot; the stylus may be positioned precisely with an alignment portion aligned with the superior margin of the humeral head, and an alignment portion aligned with the posterior margin of the humeral head. The position of the humeral head is thus adjusted precisely with respect to the cut block.

In use, the base slides over and locks to the canal reamer or tool. Before locking the base to the canal reamer or tool, version and height are set by rotating and sliding the base about the axis. When the alignment portions of the stylus are aligned with the superior and posterior margins of the humeral head, the base is locked. Once the base has been locked to the reamer or tool with the cut block at the desired version and height, the version gauge may be rotated about the base and aligned with a reference mark on the reamer or tool.

DETAILED DESCRIPTION OF THE PREFERRED EMBODIMENTS

Figure 1:
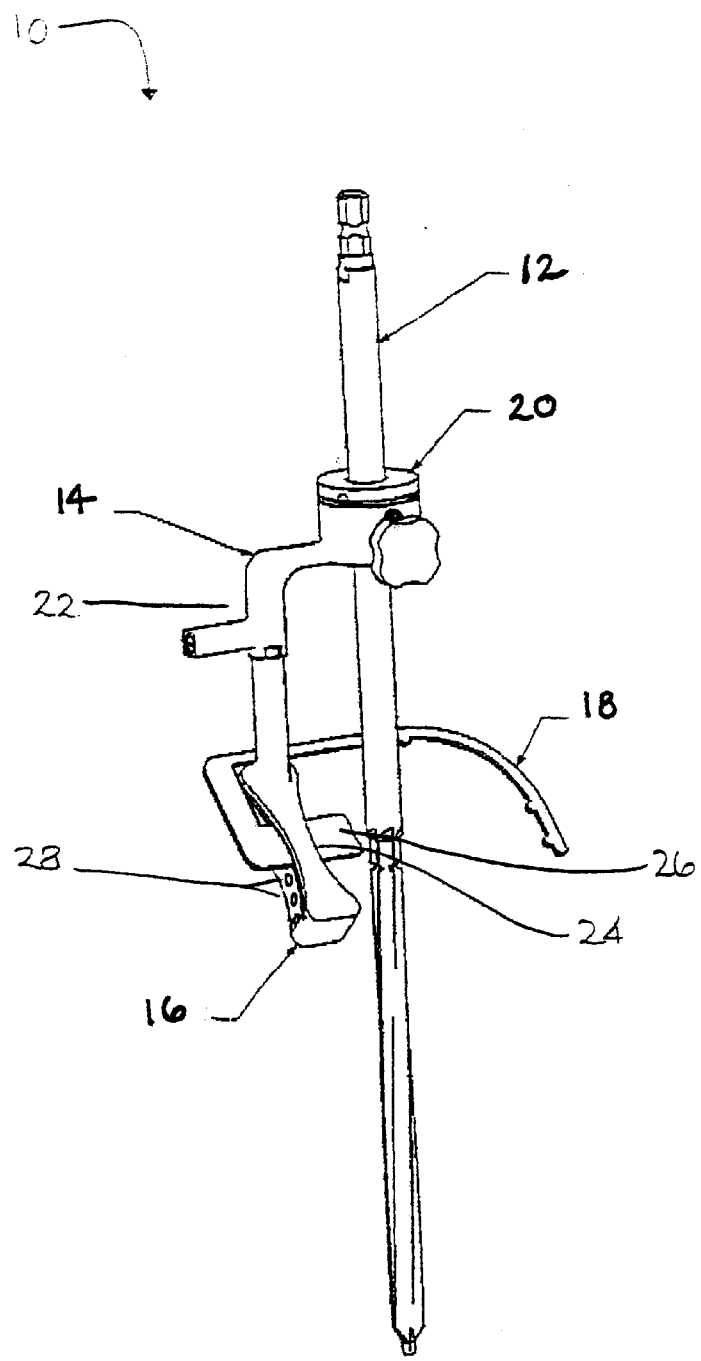
FIG. 1 is a plan view of one embodiment of a resection guide of the invention.

FIG. 1 illustrates a first embodiment of a humeral resection guide 10 for holding a cutting blade at a set angle and position for removing the humeral head in accordance with the present invention. The guide is used in connection with a reamer 12 or other tool that is inserted into the intramedullary canal of the humerus with the shank of the reamer extending superiorally above the head of the humerus to establish the axis of the humerus. Although the term reamer is used for illustrative purposes, it is noted that the tool may be any tool suitable for insertion into the intramedullary canal with a portion of the tool extending superiorally above the head of the humerus. It is not necessary that the tool have reaming capabilities.

In a preferred embodiment, the guide includes a base 14, a cut block 16, and a stylus 18. The base 14 is configured for insertion over the shank of the reamer 12. Preferably, the base 14 includes a bore for receiving the shank of the reamer to enable such insertion. The bore may extend entirely through the base or may be shallow within the base. The base 14 is rotatable about the axis of the reamer 12 so that the base 14 may be rotated slightly about the axis to provide the proper amount of humeral version. A version gauge 20 may be included to set or measure the rotation of the base 14.

The base 14 includes an outwardly and downwardly extending arm 22, the downwardly extending portion of the arm being roughly parallel to but spaced from the axis of the reamer 12. Attached to the bottom of the downwardly extending arm 22 of the base 14 is the cut block 16. Each of the cut block 16 and the base 14 include an attachment component for attaching one to the other. The attachment components may include male and female components for a taper lock, a screw attachment, male and female components for pin fixation, or any other suitable attachment. Optionally, a quick release mechanism is included to enable the cut block 16 to be separated from the base 14. The quick release mechanism may be of a ball and spring variety or any other suitable mechanism.

The cut block 16 includes a component for receiving or attaching to a surgical blade saw. Preferably, this component comprises a slot 24 for receiving the surgical blade saw. The stylus 18 is configured for attachment to the cut block 16 and extends around the articular margin of the humeral head, preferably through operable connection with the component for receiving or attaching to a surgical blade saw. Thus, the stylus 18 may include a tab 26 for receipt by the saw-receiving slot 24 of the cut block 16. The stylus 18 includes the portion for attachment to the cut block 16 and a portion extending around the articular margin of the humeral head.

The cut block 16 is further configured for fixation to the humerus. This fixation may be achieved by providing a number of small openings 28 through the cut block 16 through which pins may be inserted to fix the cut block 16 to the humerus. Once fixed, the base 14 and reamer 12 may be removed from the cut block 16.

Figure 2:
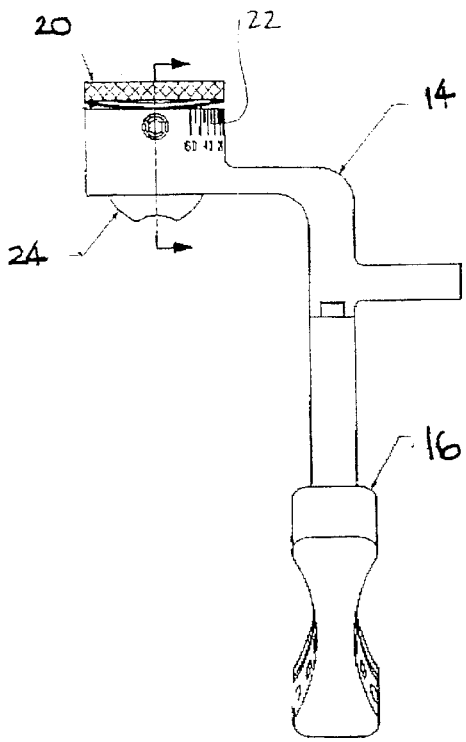
FIG. 2 is a front view of thee embodiment of FIG. 1.

As seen in FIG. 2, the version gauge 20 may reference angular markings to aid in alignment with a mark formed on the shank of the reamer 12. The reference markings may be evenly spaced numerical markings (such as 0–20–40–60) or may be

It may be desirable to mark the shank of the reamer during the surgery or the shank may be premarked with regular markings. Preferably, the version gauge 20 is a knob that rotates freely about the base. Optionally, the rotation may be restricted for movement only in measured increments.

Figure 3:
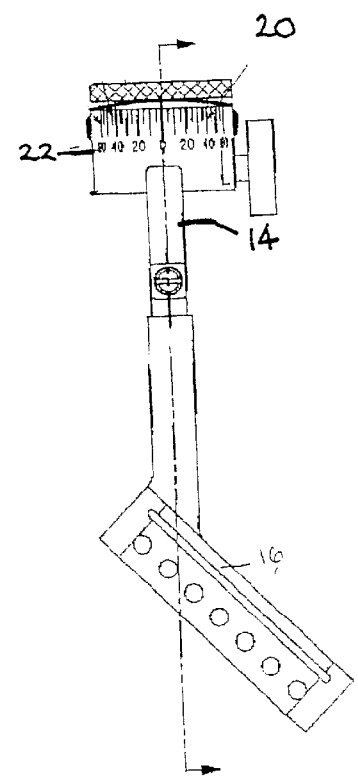
FIG. 3 is a side view of the embodiment shown in FIGS. 1 and 2.

FIG. 3 illustrates an embodiment of the guide of the present invention from another angle as shown, the markings on the version gauge 20 may reference the humeral version as determined by the styles.

Figure 4:
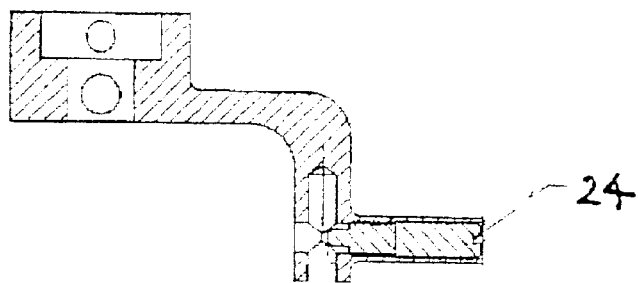
FIG. 4 is a view of a quick-release mechanism in accordance with an embodiment of the invention.

FIG. 4 depicts a quick-release ball and spring mechanism 24 that may be used for attaching the base 14 to the cut block 16.

Figure 5:
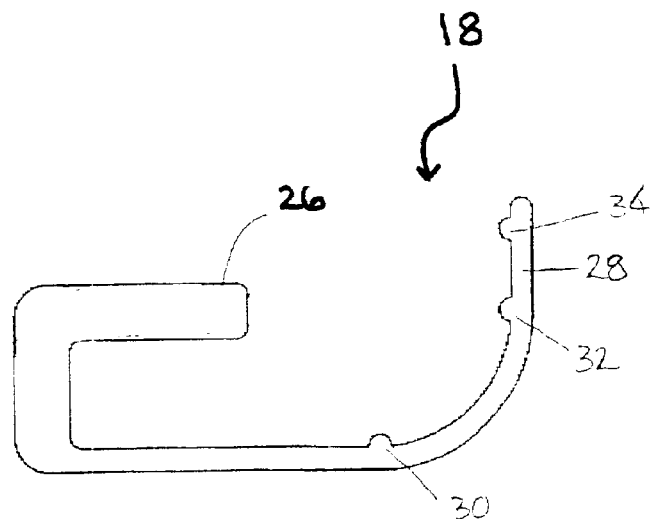
FIG. 5 is a top view of a stylus in accordance with one embodiment of the invention.

A stylus in accordance with one embodiment of the invention is shown in FIG. 5. The stylus 18 includes an attachment portion, a portion extending around the articular margin of the humeral head, and alignment portions. In a preferred embodiment, the stylus 18 is C-shaped. The stylus 18 may be made of plastic, or other suitable material. The attachment portion of the stylus 18 is configured for operative attachment to the cut block. The attachment portion may be a tab 26 that extends into the saw-receiving slot of the cut block. The position of the stylus 18 may be adjusted by adjusting the attachment of the stylus to the cut block. Thus, for example, the position of the stylus 18 may be altered by moving the 26 tab inwardly and outwardly of the saw-receiving slot. The portion 28 for extending around the articular margin of the humeral head may extend in a generally C-shaped manner and includes alignment portions, for example, fiducial tabs, for alignment with the superior and posterior margins of the humeral head. Preferably, the stylus thus includes a superior fiducial tab 30 and one or more posterior fiducial tabs 32 and 34.

The position of the humeral head may be adjusted precisely with respect to the cut block by adjusting one of the components of the guide: by rotating the base about the axis; moving the base upwardly and downwardly on the axis; and/or adjusting the position of the stylus by moving the tab inwardly and outwardly of the saw blade slot, or otherwise adjusting the attachment of the stylus to the cut block, to position the stylus precisely with a superior fiducial tab, or other alignment component, lying against the superior margin of the humeral head, and a posterior fiducial tab, or other alignment component, lying against the posterior margin of the humeral head.

In use, the base slides over and locks to the canal reamer. Before locking the base to the canal reamer, version and height are set by rotating and sliding the base about the reamer. The positioning of the stylus is adjusted by moving the tab inwardly or outwardly of the saw blade slot. When the fiducials of the stylus are aligned with the superior and posterior margins of the humeral head, the base is locked.

Once the base has been locked to the reamer with the cut block at the desired version and height, the version gauge may be rotated about the base and aligned with a reference mark on the reamer. Thus, the surgeon may acquire a quantitave measure of the humeral version. The resection may be made using the captured blade slot on the cut block.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. An apparatus for guiding the resection of the head of a humerus comprising:
    a base configured for rotatable connection with a tool defining the axis of the humerus, the tool including a portion extending superiorly above the head of the humerus, such that rotation of the base about the axis adjusts humeral version;
    a cut block operatively connected to the base and including a component for receiving a saw blade; and
    a stylus removably engaged with the cut block and configured to extend around the articular margin of the humeral head for alignment with the superior and posterior margins of the humeral head.

2. The apparatus of claim 1, wherein the base is configured for insertion over the portion of the tool extending superiorally above the head of the humerus.

3. The apparatus of claim 1, wherein the base includes a bore for receipt of the portion of the tool extending superiorally above the head of the humerus.

4. The apparatus of claim 1, and further including a version gauge connected to the base, the version gauge configured for selling or measuring the rotation of the base.

5. The apparatus of claim 4, wherein the version gauge includes markings for alignment with markings on the tool defining the axis of the humerus.

6. The apparatus of claim 4, wherein the version gauge is a knob that rotates freely about the base.

7. The apparatus of claim 1, wherein the base includes an outwardly and downwardly extending arm, the downwardly extending portion of the arm being roughly parallel to but spaced from the axis of the humerus as defined by the tool, the cut block being operatively connected to the arm.

8. The apparatus of claim 1, wherein the component for receiving a saw blade is a saw-receiving slot.

9. The apparatus of claim 8, wherein the position of the stylus may be adjusted by adjusting an attachment of the stylus to the cut block.

10. The apparatus of claim 8, wherein the stylus includes a tab for receipt by the saw-receiving slot.

11. The apparatus of claim 10, wherein the attachment is adjusted by moving the tab inwardly and outwardly of the saw-receiving slot.

12. The apparatus of claim 1, wherein the cut block is configured for fixation to the humerus.

13. The apparatus of claim 1, wherein the cut block includes a plurality of small openings through which pins may be inserted to fix the cut block to the humerus.

14. The apparatus of claim 1, wherein the base includes a knob for locking the base to a canal reamer.

15. The apparatus of claim 1, wherein the stylus is generally c-shaped.

16. The apparatus of claim 1, wherein the stylus includes alignment portions for alignment with the superior and posterior margins of the humeral head.

17. The apparatus of claim 16, wherein the alignment portions are tabs.

18. The apparatus of claim 1, wherein the operative connection of the cut block to the base includes a quick-release mechanism.

19. The apparatus of claim 18, wherein the quick release mechanism of a ball and spring variety.

20. The apparatus of claim 1, wherein the tool for defining the axis of the humerus is a canal reamer.

21. An apparatus for guiding the resection of the head of a humerus, said humerus having an outer perimeter, comprising:

a base configured for rotatable connection with a tool defining the axis of the humerus, the tool including a portion extending superiorly above the head of the humerus, such that rotation of the base about the axis adjusts humeral version;

a cut block operatively connected to the base and including a component for receiving a saw blade;

and a stylus removably engaged with the cut block and configured to extend around the outer perimeter of the humeral head for alignment with the superior and posterior margins of the humeral head.

22. An apparatus for guiding the resection of the head of a humerus, comprising:

a base configured for rotatable connection with a tool defining the axis of the humerus, the tool including a portion extending superiorly above the head of the humerus, such that rotation of the base about the axis adjusts humeral version;

a cut block operatively connected to the base and including a component for receiving a saw blade, said cut block having a predetermined angle with respect to said apparatus for resecting said humeral head;

and a stylus removably engaged with the cut block and configured to align with the superior and posterior margins of the humeral head.

23. An apparatus for guiding the resection of the head of a humerus comprising:

a base configured for rotatable connection with a tool defining the axis of the humerus, the tool including a portion extending superiorly above the head of the humerus, such that rotation of the base about the axis adjusts humeral version;

a cut block operatively connected to the base and including a component for receiving a saw blade; and a stylus removably engaged with the cut block and configured to extend around the articular margin of the humeral head for alignment with the superior and posterior margins of the humeral head; wherein the stylus includes a tab for receipt by the component for receiving a saw blade.

24. The apparatus according to claim 23 wherein the component for receiving a saw blade comprises a saw-receiving slot.

* * * * *